United States Patent
Mizuno et al.

(10) Patent No.: US 11,192,855 B2
(45) Date of Patent: Dec. 7, 2021

(54) METHOD FOR MANUFACTURING METHIONINE

(71) Applicant: SUMITOMO CHEMICAL COMPANY, LIMITED, Chuo-ku (JP)

(72) Inventors: Takao Mizuno, Niihama (JP); Daisuke Yamashita, Niihama (JP); Yoshiyuki Koizumi, Niihama (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 0 days.

(21) Appl. No.: 16/954,705

(22) PCT Filed: Dec. 18, 2018

(86) PCT No.: PCT/JP2018/046554
§ 371 (c)(1),
(2) Date: Jun. 17, 2020

(87) PCT Pub. No.: WO2019/124370
PCT Pub. Date: Jun. 27, 2019

(65) Prior Publication Data
US 2021/0087139 A1    Mar. 25, 2021

(30) Foreign Application Priority Data
Dec. 19, 2017   (JP) .............................. JP2017-242874

(51) Int. Cl.
*C07C 319/28* (2006.01)
*C07C 319/20* (2006.01)
*C07C 319/12* (2006.01)

(52) U.S. Cl.
CPC .......... *C07C 319/28* (2013.01); *C07C 319/20* (2013.01); *C07C 319/12* (2013.01)

(58) Field of Classification Search
CPC ............................ C07C 319/28; C07C 319/20
See application file for complete search history.

(56) References Cited

U.S. PATENT DOCUMENTS

| | | | | |
|---|---|---|---|---|
| 7,655,072 | B2 * | 2/2010 | Hasselbach | ........... C07C 319/20 95/235 |
| 2013/0245318 | A1 * | 9/2013 | Steffan | .................. C07C 319/20 562/531 |
| 2014/0155652 | A1 | 6/2014 | Yamashiro et al. | |
| 2015/0284323 | A1 | 10/2015 | Chen et al. | |
| 2018/0111899 | A1 | 4/2018 | Capelle et al. | |

FOREIGN PATENT DOCUMENTS

| | | |
|---|---|---|
| CN | 1946468 A | 4/2007 |
| CN | 102659650 A | 9/2012 |
| CN | 103724242 A | 4/2014 |
| CN | 103848765 A | 6/2014 |
| JP | 2006-206534 A | 8/2006 |
| JP | 2014-108956 A | 6/2014 |
| JP | 2015-526485 A | 9/2015 |
| WO | WO 2016/170252 A1 | 10/2016 |

OTHER PUBLICATIONS

International Search Report dated Mar. 19, 2019 in PCT/JP2018/046554 (submitting English translation only), 2 pages.
International Preliminary Report on Patentability dated Jun. 23, 2020 in PCT/JP2018/046554 (submitting English translation only), 5 pages.
Extended European Search Report dated Aug. 25, 2021 in European Patent Application No. 18891079.8, 4 pages.
Office Action dated Sep. 9, 2021, in Chinese Application No. 201880081501.3 (w/ English translation) citing References AO and AP.

* cited by examiner

*Primary Examiner* — Rosalynd A Keys
(74) *Attorney, Agent, or Firm* — Oblon, McClelland, Maier & Neustadt, L.L.P.

(57) ABSTRACT

An object of the present invention is to provide a method for manufacturing methionine capable of achieving an improvement in ammonia removal efficiency. The manufacturing method of the present invention comprises a removal step of supplying a liquid containing a methionine salt, which is obtained by reacting 3-methylmercaptopropionaldehyde and hydrocyanic acid, or a compound obtained by reacting 3-methylmercaptopropionaldehyde and hydrocyanic acid, with carbon dioxide and ammonia to obtain a liquid containing 5-(2-methylmercaptoethyl)hydantoin and then hydrolyzing the 5-(2-methylmercaptoethyl)hydantoin, to a diffusion tower from an upper portion thereof while supplying a stripping gas to the diffusion tower from a lower portion thereof to remove ammonia contained in the liquid through stripping, and the stripping gas contains a process gas generated in a process of manufacturing methionine.

3 Claims, 1 Drawing Sheet

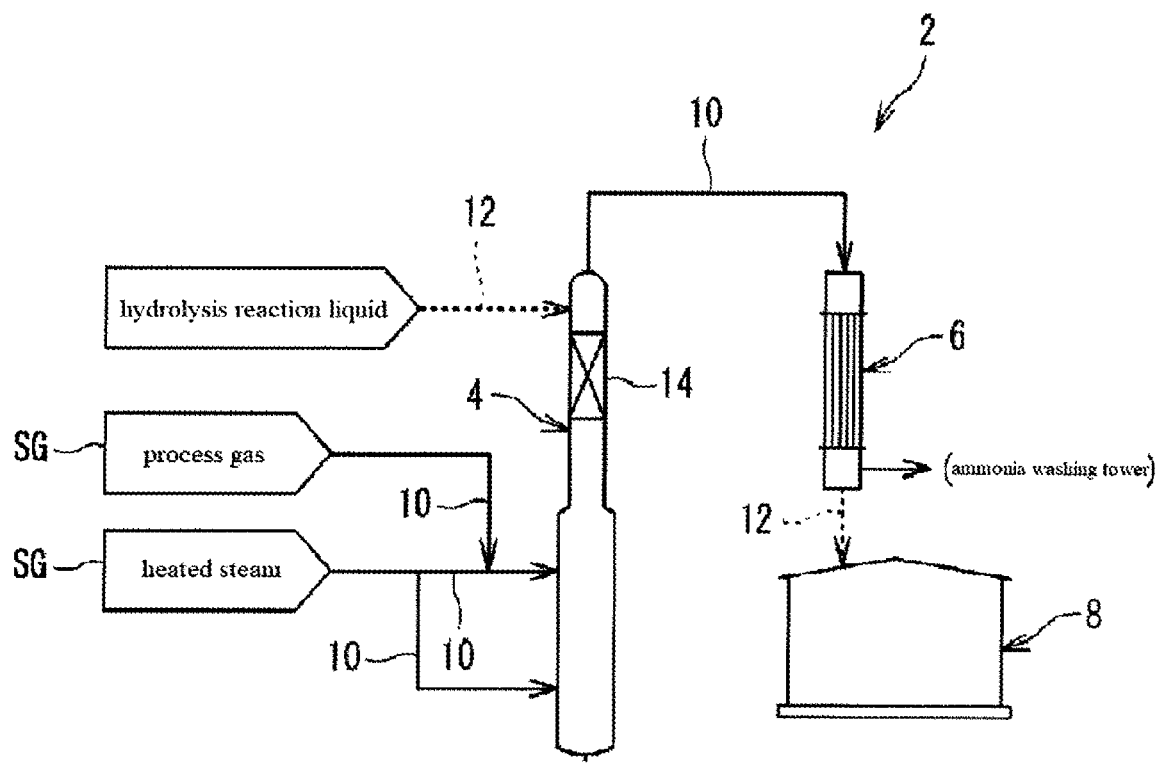

METHOD FOR MANUFACTURING METHIONINE

TECHNICAL FIELD

This patent application claims priority under the Paris Convention based on Japanese Patent Application No. 2017-242874 (filed on Dec. 19, 2017) incorporated herein by reference in its entirety.

The present invention relates to a method for manufacturing methionine.

BACKGROUND ART

In a method for manufacturing methionine, 5-(2-methylmercaptoethyl)hydantoin (hereinafter also referred to as methionine hydantoin) is prepared. This methionine hydantoin is obtained by a method of reacting 3-methylmercaptopropionaldehyde cyanohydrin (hereinafter also referred to as methionine cyanohydrin) with carbon dioxide and ammonia in water, for example. This methionine hydantoin can also be obtained by a method of reacting 3-methylmercaptopropionaldehyde (hereinafter also referred to as methionine aldehyde) with hydrocyanic acid, carbon dioxide and ammonia.

In this manufacturing method, methionine hydantoin is hydrolyzed. As a result, a methionine salt is obtained. In this manufacturing method, carbon dioxide is blown into a reaction liquid obtained by the hydrolysis reaction to neutralize the reaction liquid and precipitate methionine.

An excess amount of ammonia is used in the reaction for obtaining methionine hydantoin described above. Therefore, the reaction liquid obtained by the hydrolysis reaction contains not only the methionine salt but also ammonia. When methionine is precipitated while the reaction liquid contains ammonia, acid used for neutralization may be required in a large amount, or an ammonium salt mixed in a methionine product may reduce yield, purity, etc. Therefore, it is preferable that the amount of ammonia contained in the reaction liquid be as small as possible.

Due to such circumstances, various studies have been conducted on a technique of removing ammonia from reaction liquid obtained by the hydrolysis reaction described above (e.g., Patent Document 1).

In Patent Document 1, stripping (hereinafter also referred to as steam stripping) with steam prepared by using a boiler etc. (hereinafter also referred to as heated steam) is considered for a technique for removing ammonia contained in the reaction liquid described above.

PRIOR ART DOCUMENT

Patent Document

Patent Document 1: Japanese Laid-Open Patent Publication No. 2006-206534

SUMMARY OF THE INVENTION

Problem to be Solved by the Invention

Although ammonia can be removed from the reaction liquid described above by the steam stripping disclosed in Patent Document 1 described above, a demand exists for development of a technique capable of removing ammonia more efficiently than this steam stripping.

The present invention was conceived in view of the situations, and an object thereof is to provide a method for manufacturing methionine capable of achieving an improvement in ammonia removal efficiency.

Means for Solving Problem

Focusing attention on the fact that a method for manufacturing methionine comprises many steps associated with discharge of a gas and intensively studying a technique capable of achieving an improvement in ammonia removal efficiency, the present inventors consequently found that ammonia removal efficiency can be improved by replacing heated steam used in stripping with a gas discharged in a process of manufacturing methionine, thereby completing the present invention. Therefore, a method for manufacturing methionine according to the present invention is a method for manufacturing methionine comprising a hydantoin step of reacting 3-methylmercaptopropionaldehyde and hydrocyanic acid, or a compound obtained by reacting 3-methylmercaptopropionaldehyde and hydrocyanic acid, with carbon dioxide and ammonia to obtain a liquid containing 5-(2-methylmercaptoethyl)hydantoin, a hydrolysis step of hydrolyzing the 5-(2-methylmercaptoethyl)hydantoin to obtain a liquid containing a methionine salt, a crystallization step of introducing carbon dioxide into the liquid containing a methionine salt to precipitate methionine, and a separation step of performing solid-liquid separation of a methionine slurry obtained in the crystallization step into a cake of the methionine and a mother liquor, the method comprising:

a removal step of supplying the liquid containing a methionine salt obtained in the hydrolysis step to a diffusion tower from an upper portion thereof and supplying a stripping gas to the diffusion tower from a lower portion thereof to remove ammonia contained in the liquid through stripping, wherein the stripping gas contains a process gas generated in a process of manufacturing methionine.

In this method for manufacturing methionine, ammonia is removed from the liquid containing a methionine salt obtained in the hydrolysis step (hereinafter also referred to as a hydrolysis reaction liquid) by using the stripping gas containing the process gas generated in the process of manufacturing methionine. The stripping using this stripping gas is improved in ammonia removal efficiency as compared to conventional stripping using only heated steam. Since this process gas is a gas inevitably generated in the process of manufacturing methionine, the amount of the heated steam used can be reduced by using this process gas. This manufacturing method can achieve an improvement in the ammonia removal efficiency and moreover can reduce the amount of the heated steam used.

Preferably, this manufacturing method comprises a bubbling step of blowing an inert gas into the liquid containing 5-(2-methylmercaptoethyl)hydantoin, and a concentration step of concentrating the mother liquor, and the stripping gas contains at least one process gas selected from the group consisting of a process gas generated in the bubbling step, a process gas generated in the concentration step, and a process gas generated in the hydrolysis step. Such a configuration contributes to stable securement of process gas. In this manufacturing method, the process gas can stably be used in the stripping, so that the ammonia removal efficiency can be improved. From the viewpoint of stably securing the process gas and improving the ammonia removal efficiency, the stripping gas more preferably contains the process gas generated in the concentration step.

Effect of the Invention

As is clear from the above description, the manufacturing method of the present invention can achieve an improvement in ammonia removal efficiency. Moreover, this manufacturing method can reduce the amount of heated steam used.

BRIEF DESCRIPTION OF DRAWINGS

FIG. 1 is a schematic showing a portion of a facility used in a method for manufacturing methionine according to an embodiment of the present invention.

MODE FOR CARRYING OUT THE INVENTION

The present invention will now be described in detail based on a preferred embodiment with appropriate reference to the drawing. In this description, conventionally known portions will not be described in detail except those necessary for describing the present invention.

Method for Manufacturing Methionine

In the method for manufacturing methionine according to an embodiment of the present invention, methionine aldehyde is used as a starting material to obtain methionine. This manufacturing method comprises hydantoin step, a hydrolysis step, a crystallization step, a separation step, a bubbling step, a concentration step, and a removal step. Methionine aldehyde can be obtained by reacting methyl mercaptan and acrolein, for example.

Hydantoin Step

In the hydantoin step, methionine aldehyde and hydrocyanic acid, or a compound obtained by reacting these components, for example, methionine cyanohydrin, are reacted with carbon dioxide and ammonia in the presence of water to obtain a liquid containing methionine hydantoin. Specifically, examples of a method for obtaining a liquid containing methionine hydantoin (hereinafter also referred to as a hydantoin liquid) comprise a method of reacting methionine aldehyde, hydrocyanic acid, carbon dioxide, and ammonia, and a method of reacting methionine cyanohydrin, carbon dioxide, and ammonia. In the present invention, carbon dioxide may be present in the form of carbonate ions and/or hydrogencarbonate ions. Ammonia may be present also in the form of ammonium ions.

The reaction for obtaining methionine hydantoin from methionine cyanohydrin can be performed by mixing methionine cyanohydrin with water in which carbon dioxide and ammonia are dissolved and heating the water, for example. The reaction temperature is usually 50 to 90° C. The reaction time is usually 0.5 to 6 hours.

In the reaction for obtaining methionine hydantoin from methionine cyanohydrin, an amount of water used is usually 3 to 4 times by weight an amount of methionine cyanohydrin.

An amount of carbon dioxide used is usually 1 to 5 mol, preferably 1.5 to 3 mol, per mol of methionine cyanohydrin.

An amount of ammonia used is usually an excess amount of more than 2 mol, preferably 3 to 5 mol, per mol of methionine cyanohydrin.

When ammonium carbonate is used instead of carbon dioxide and ammonia, an amount of ammonium carbonate used is usually 0.7 to 3 times by weight, preferably 0.9 to 2 times by weight an amount of methionine cyanohydrin.

A methionine hydantoin concentration of the hydantoin liquid is usually 1 to 50 mass %, preferably 10 to 20 mass %. In the present invention, the methionine hydantoin concentration can be measured by liquid chromatography.

In the hydantoin step, an excess amount of ammonia is usually used. Therefore, unreacted ammonia remains in the hydantoin liquid. This hydantoin liquid contains ammonia. An ammonia concentration of this hydantoin liquid is usually 2 to 7 mass %, preferably 3 to 6 mass %. An amount of ammonia contained in the hydantoin liquid is usually 1 to 4 mol, preferably 2 to 3 mol, per mol of methionine hydantoin. In the present invention, the ammonia concentration is measured by gas chromatography. Analysis conditions for measuring the ammonia concentration are as follows.

Gas Chromatography Analysis Conditions

Column packing: HayeSep C 80/100 mesh
Column: 2 m in length
Carrier gas flow rate: helium, 80 mL/min
Detector: thermal conductivity detector (TCD)

The hydantoin liquid usually contains carbon dioxide in addition to ammonia. A carbon dioxide concentration of this hydantoin liquid is usually 2 to 7 mass %. The carbon dioxide concentration can be measured by gas chromatography.

In the reaction for obtaining methionine hydantoin (hereinafter also referred to as a hydantoin reaction), methyl mercaptan is generated as a decomposition product. Therefore, the hydantoin liquid may contain a slight amount of methyl mercaptan. When the hydantoin liquid contains methyl mercaptan, a concentration of methyl mercaptan contained in the hydantoin liquid is usually 0.001 mass % to 1 mass %.

Hydrolysis Step

In the hydrolysis step, the methionine hydantoin obtained in the hydantoin step is hydrolyzed in the presence of an alkaline compound such as potassium hydroxide, sodium hydroxide, potassium carbonate, and potassium hydrogencarbonate. As a result, a liquid containing a methionine salt (hereinafter also referred to as a hydrolysis reaction liquid) is obtained. In the hydrolysis step, the pressure is usually set in a range of about 0.5 to 1.0 MPaG. The temperature is usually set in a range of 150 to 200° C. The hydrolysis reaction liquid contains ammonia, and the ammonia concentration of the hydrolysis reaction liquid is usually 0.2 to 1 mass %. This ammonia concentration is measured by the gas chromatography described above.

In the hydrolysis step, the hydantoin liquid is heated in a reaction tank. Since the hydantoin liquid contains water, steam is distilled from the hydantoin liquid by the heating. In other words, a gas mainly composed of steam is generated in this hydrolysis reaction. Since ammonia and carbon dioxide are generated by the hydrolysis of methionine hydantoin, this gas contains ammonia and carbon dioxide in addition to steam.

Crystallization Step

In the crystallization step, carbon dioxide is introduced into the hydrolysis reaction liquid obtained in the hydrolysis step. As a result, methionine is precipitated, and a methionine slurry is obtained. In the crystallization step, the crystallization temperature is usually 0 to 50° C., preferably 10 to 30° C. The crystallization time is basically time until carbon dioxide is saturated in the reaction liquid so that methionine is sufficiently precipitated and is usually 30 minutes to 24 hours.

Separation Step

In the separation step, the methionine slurry obtained in the crystallization step is subjected to solid-liquid separation into a methionine cake that is a solid component and a mother liquor that is a liquid component by a solid-liquid separator such as a centrifuge. In this manufacturing method, usually, the methionine cake obtained in this separation step is washed with washing water for purification, and the cake is then dried to obtain powder methionine as a product.

Bubbling Step

In this manufacturing method, the bubbling step is suitably performed before the hydrolysis step. In this bubbling step, an inert gas is blown into the hydantoin liquid obtained in the hydantoin step. As described above, the hydantoin liquid usually contains ammonia and carbon dioxide. Therefore, by blowing the inert gas into the hydantoin liquid, ammonia and carbon dioxide are diffused from the hydantoin liquid. As a result, the inert gas, ammonia and carbon dioxide are discharged in this bubbling step. As described above, the hydantoin liquid may contain a slight amount of methyl mercaptan. In this case, this methyl mercaptan is also diffused from the hydantoin liquid by blowing the inert gas, so that methyl mercaptan is also discharged.

Examples of the inert gas blown in this bubbling step comprise nitrogen gas, air, etc. An amount of the inert gas blown is usually 5 to 200 kg, preferably 10 to 100 kg, more preferably 20 to 60 kg per hour per 1000 kg of the hydantoin liquid.

In this bubbling step, from the viewpoint that the inert gas can be dispersed as fine bubbles in the hydantoin liquid, the blowing of the inert gas is preferably performed by using a sparger etc.

The temperature of the hydantoin liquid at the time of blowing of the inert gas is usually 30 to 70° C., preferably 40 to 60 The pH of this hydantoin liquid is usually 9 to 14. The time of blowing of the inert gas is usually 200 to 1200 minutes, preferably 400 to 800 minutes.

Concentration Step

As described above, in this manufacturing method, the methionine slurry is subjected to solid-liquid separation to obtain the mother liquor as the liquid component. Methionine and potassium bicarbonate are usually dissolved in this mother liquor. Methionine and potassium bicarbonate are valuable components in the manufacturing of methionine. Therefore, in the concentration step, to recover methionine and potassium bicarbonate, the mother liquor is heated, and components such as water contained in this mother liquor are evaporated to concentrate the mother liquor. In this concentration step, the heating temperature of the mother liquor is usually 100 to 140° C.

As described above, in this concentration step, the components such as water contained in the mother liquor are evaporated due to the concentration of the mother liquor. In other words, a gas mainly composed of steam is generated in the concentration step. Since carbon dioxide is blown in in the crystallization step, the mother liquor contains carbon dioxide. Therefore, the gas generated due to the concentration of the mother liquor contains carbon dioxide. If ammonia remains in the mother liquor, the gas generated due to the concentration of the mother liquor contains ammonia.

Process Gas

In the present invention, a gas generated in the process of manufacturing of methionine, in other words, gas generated by a reaction or a treatment in each step comprised in the method for manufacturing methionine, is referred to as a process gas.

In the bubbling step, a gas mainly composed of an inert gas, or specifically, a gas containing an inert gas, ammonia, and carbon dioxide, is generated by the treatment of blowing the inert gas into the hydantoin liquid. When the hydantoin liquid contains a slight amount of methyl mercaptan, a gas containing the inert gas, ammonia, carbon dioxide, and methyl mercaptan is generated in the bubbling step. In this manufacturing method, the gas generated by the treatment of blowing the inert gas into the hydantoin liquid is a process gas and is particularly referred to as a bubbling process gas.

In the hydrolysis step, a gas mainly composed of steam, or specifically, a gas containing steam, ammonia, and carbon dioxide, is generated by the hydrolysis reaction of methionine hydantoin. In this manufacturing method, the gas generated by the hydrolysis reaction of methionine hydantoin is a process gas and is particularly referred to as a hydrolysis process gas.

In the concentration step, a gas mainly composed of steam, or specifically, a gas containing steam and carbon dioxide, is generated by the treatment of concentrating the mother liquor. When ammonia remains in the mother liquor, a gas containing steam, carbon dioxide, and ammonia is generated in the concentration step. In this manufacturing method, the gas generated by the treatment of concentrating the mother liquor is a process gas and is particularly referred to as a concentration process gas.

Removal Step

The hydrolysis reaction liquid described above usually contains ammonia. Therefore, ammonia is removed from the hydrolysis reaction liquid so as to efficiently precipitate methionine. In this manufacturing method, stripping is performed for the hydrolysis reaction liquid so as to remove ammonia from the hydrolysis reaction liquid.

FIG. 1 shows a portion of a facility 2 used in the method for manufacturing methionine according to an embodiment of the present invention. In this manufacturing method, the stripping of the hydrolysis reaction liquid is performed by using this facility 2. This facility 2 comprises a diffusion tower 4, an emission gas condenser 6, and a storage tank 8. The diffusion tower 4 and the emission gas condenser 6 are connected by a gas pipe 10 through which gas flows. The emission gas condenser 6 and the storage tank 8 are connected by a liquid pipe 12 through which liquid flows. In this facility 2, a packed tower is used as the diffusion tower 4. In this facility 2, a plate tower may be used as the diffusion tower 4.

In this manufacturing method, the hydrolysis reaction liquid is supplied through the liquid pipe 12 to an upper portion of the diffusion tower 4.

An amount of the hydrolysis reaction liquid supplied to the diffusion tower 4 is usually set appropriately within a range of 10 to 100 t/h. The hydrolysis reaction liquid supplied to the diffusion tower 4 is discharged through the liquid pipe 12 connected to a bottom portion. The hydrolysis reaction liquid discharged from the diffusion tower 4 is supplied to a reaction tank (not shown) for performing the crystallization step.

The diffusion tower 4 is configured such that a constant amount of the hydrolysis reaction liquid is retained in the bottom portion of the diffusion tower 4 by adjusting the supply amount and the discharge amount of the hydrolysis reaction liquid. In the present invention, a portion of the hydrolysis reaction liquid retained in the bottom portion of the diffusion tower 4 is referred to as a liquid phase part, and a portion on the upper side of this liquid phase part is referred to as a gas phase part. Therefore, the liquid phase part made up of the hydrolysis reaction liquid and the gas phase part are formed in a lower portion of the diffusion tower 4. In the diffusion tower 4, the supply amount and the discharge amount of the hydrolysis reaction liquid are adjusted such that a boundary (not shown) between the liquid phase part and the gas phase part, i.e., a liquid surface, is formed at a constant position.

The stripping is performed by using a gas. The gas used for the stripping is referred to as a stripping gas SG.

In this manufacturing method, the stripping gas SG is supplied through the gas pipe 10 to the lower portion of the diffusion tower 4. In the diffusion tower 4, the stripping gas SG is supplied to each of the liquid phase part and the gas phase part. The stripping gas SG moves inside the diffusion tower 4 from the lower portion toward the upper portion. The stripping gas SG is discharged from a top portion of the diffusion tower 4.

In this manufacturing method, the hydrolysis reaction liquid is supplied to the upper portion of the diffusion tower 4 while the stripping gas SG is blown into the lower portion to remove ammonia from the hydrolysis reaction liquid by stripping.

As described above, the hydrolysis reaction liquid discharged from the diffusion tower 4 is supplied to the reaction tank (not shown) for performing the crystallization step. In this manufacturing method, the ammonia concentration of the hydrolysis reaction liquid discharged from the diffusion tower 4 is lower than the ammonia concentration of the hydrolysis reaction liquid supplied to the diffusion tower 4. Specifically, the reaction tank for performing crystallization is supplied with the hydrolysis reaction liquid from which ammonia has been removed.

In this manufacturing method, the ammonia concentration of the stripping gas SG discharged from the top portion of the diffusion tower 4 is higher than the ammonia concentration of the stripping gas SG supplied to the lower portion of the diffusion tower 4. Specifically, in this manufacturing method, the stripping gas SG having ammonia recovered therein from the hydrolysis reaction liquid is discharged from the top portion of the diffusion tower 4. In this manufacturing method, the stripping gas SG discharged from the top portion of the diffusion tower 4 is supplied to the emission gas condenser 6. In the emission gas condenser 6, the stripping gas SG having ammonia recovered therein is condensed and cooled and is supplied as ammonia water to the storage tank 8. In this storage tank 8, the ammonia water is used for adjusting ammonium carbonate water for the hydantoin reaction. Uncondensed ammonia etc. in the emission gas condenser 6 is supplied as an emission gas to an ammonia washing tower (not shown), and ammonia is recovered from the emission gas in this washing tower.

A retention time of the hydrolysis reaction liquid in a rectification part 14 of the diffusion tower 4 affects an ammonia removal efficiency and a throughput. In this manufacturing method, from the viewpoint of improving the ammonia removal efficiency and ensuring the throughput, the hydrolysis reaction liquid is supplied such that the retention time of the hydrolysis reaction liquid in the rectification part 14 of the diffusion tower 4 is usually in a range of 10 to 120 seconds, preferably 20 seconds or more and 100 seconds or less, more preferably 70 seconds or less.

Although the retention time of the hydrolysis reaction liquid in the rectification part 14 can be estimated as an approximate value from a porosity and a packing volume of a packing material in the case of a packed tower or from a structure etc. of a plate in the case of a plate tower, more precisely, by stopping the supply of the hydrolysis reaction liquid and the stripping gas SG after the stripping reaches a steady state to obtain as a retained liquid amount a liquid amount at a tower bottom increased due to the hydrolysis reaction liquid flowing down from the rectification part 14, the retention time can be obtained from this retained liquid amount and the supply amount. The retention time can be obtained by measuring the retained liquid amount.

In this manufacturing method, the stripping is performed with the supply amount of the hydrolysis reaction liquid and/or the stripping gas SG adjusted such that an amount of a distillate obtained by cooling the stripping gas SG discharged from the top portion of the diffusion tower 4, i.e., an amount of distillation from the diffusion tower 4, becomes constant.

Although the supply amount can be adjusted by measuring the amount of distillation, the supply amount is usually adjusted so that the temperature of the upper portion of the diffusion tower 4 becomes constant.

In this manufacturing method, from the viewpoint of a balance between the ammonia removal efficiency and the energy required for removal, the amount of distillation from the diffusion tower 4 is usually 2 to 10 mass %, preferably 3 to 7 mass % of the amount of the hydrolysis reaction liquid supplied to the diffusion tower 4.

Stripping Gas SG

As described above, in this manufacturing method, the hydrolysis process gas is generated in the hydrolysis step. The bubbling process gas is generated in the bubbling step. Furthermore, the concentration process gas is generated in the concentration step. In this manufacturing method, the hydrolysis process gas, the bubbling process gas, and the concentration process gas are process gases generated in the process of manufacturing methionine and can be used as the stripping gas SG described above. As shown in FIG. 1, the process gases are supplied to the lower portion of the diffusion tower 4. In this manufacturing method, the temperature of the process gases is usually 100 to 150° C. The pressure of the process gas is usually 0 to 0.3 MPaG.

As shown in FIG. 1, the facility 2 is configured such that heated steam can be supplied as the stripping gas SG to the lower portion of the diffusion tower 4. In this manufacturing method, the stripping gas SG can contain heated steam in addition to the process gases described above. In this case, the temperature of the heated steam is usually 100 to 180° C. The pressure of the heated steam is usually 0 to 0.7 MPaG.

In this method for manufacturing methionine, ammonia is removed from the hydrolysis reaction liquid by using the stripping gas SG containing a process gas generated in the process of manufacturing methionine. The stripping using this stripping gas SG is improved in the ammonia removal efficiency as compared to conventional stripping using only heated steam. Since this process gas is a gas inevitably generated in the process of manufacturing methionine, the amount of the heated steam used can be reduced by using this process gas. This manufacturing method can achieve an improvement in the ammonia removal efficiency and moreover can reduce the amount of the heated steam used.

In this manufacturing method, the stripping gas SG preferably contains at least one process gas selected from the group consisting of the bubbling process gas, the concentration process gas, and the hydrolysis process gas. Such a configuration contributes to stable securement of the process gas. In this manufacturing method, the process gas can stably be used in the stripping, so that the ammonia removal efficiency can be improved. From the viewpoint of stably securing the process gas and improving the ammonia removal efficiency, the stripping gas SG more preferably contains the concentration process gas.

In this manufacturing method, if the supply amount of the stripping gas SG is insufficient when only the process gas is used, the stripping gas SG can contain heated steam. In this case, from the viewpoint of the ammonia removal efficiency, the proportion of the amount of the process gas to the total amount of stripping gas SG is usually 10 mass % or more, preferably 15 mass % or more, more preferably 20 mass % or more, further preferably 25 mass % or more.

As shown in FIG. 1, in the facility 2 for the method for manufacturing methionine according to an embodiment of the present invention, the stripping gas SG is supplied to the lower portion of the diffusion tower 4. Particularly, in this facility 2, the stripping gas SG is supplied to each of the liquid phase part and the gas phase part formed in the lower portion of the diffusion tower 4. In this manufacturing method, since the stripping gas SG is supplied not only to the gas phase part but also to the liquid phase part, the stripping of the hydrolysis reaction liquid is effectively performed as compared to when the stripping gas SG is supplied only to the gas phase part or the liquid phase part. This manufacturing method can achieve an improvement in the ammonia removal efficiency.

In this manufacturing method, the stripping gas SG is preferably supplied to each of the liquid phase part and the gas phase part formed in the lower portion of the diffusion tower 4. As a result, the ammonia removal efficiency can be improved. From this viewpoint, in this manufacturing method, more preferably, the process gas and the heated steam are used as the stripping gas SG to supply the heated steam to the liquid phase part and to supply only the process gas, or both the process gas and the heated steam, to the gas phase part. In this case, the proportion of the amount of the heated steam supplied to the liquid phase part relative to the total amount of stripping gas SG is preferably 10 mass % to 30 mass %. Particularly, in this manufacturing method, from the viewpoint of improving the ammonia removal efficiency, the proportion of the amount of the process gas relative to the total amount of the stripping gas SG supplied to the gas phase part is preferably 10 mass % or more.

In this manufacturing method, further preferably, the process gas and the heated steam are used as the stripping gas SG to supply the heated steam to the liquid phase part and to supply both the process gas and the heated steam to the gas phase part. As a result, the ammonia removal efficiency can further be improved. As described above, in this manufacturing method, the hydrolysis reaction liquid is supplied from the upper portion of the diffusion tower 4. From the viewpoint of further improving the ammonia removal efficiency, the amount of the process gas supplied to the gas phase part is preferably 1 mass % to 10 mass % of the amount of the hydrolysis reaction liquid supplied to the upper portion of the diffusion tower. The amount of the heated steam supplied to the gas phase part is preferably 0.5 mass % to 5 mass % of the amount of the hydrolysis reaction liquid supplied. The amount of the heated steam supplied to the liquid phase part is preferably 0.5 mass % to 5 mass % of the amount of the hydrolysis reaction liquid supplied.

As is clear from the above description, the manufacturing method of the present invention can achieve an improvement in the ammonia removal efficiency. Moreover, this manufacturing method can reduce the amount of the heated steam used.

EXAMPLES

The present invention will hereinafter be described in more detail with examples etc.; however, the present invention is not limited only to these examples.

Example 1

Manufacturing of Methionine

Methionine aldehyde and hydrocyanic acid were reacted at normal temperature under ordinary pressure to synthesize methionine cyanohydrin. Ammonium carbonate was reacted with this methionine cyanohydrin in water at 75° C. for 2.5 hours to obtain a hydantoin liquid containing 15 mass % methionine hydantoin and 3.6 mass % ammonia.

A nitrogen gas was blown into the hydantoin liquid as an inert gas.

A liquid (potassium concentration: about 7.5 mass %) obtained by mixing a basic potassium compound containing potassium carbonate, potassium hydrogencarbonate, and potassium hydroxide with the hydantoin liquid after the blowing of the nitrogen gas was continuously supplied from an upper portion of an autoclave (supply rate: 700 g/hour), and a hydrolysis reaction was performed while maintaining the pressure at 1.0 MPaG and the temperature at 180° C. to obtain a liquid containing a methionine salt (hereinafter referred to as a hydrolysis reaction liquid).

Stripping was performed for the hydrolysis reaction liquid. The stripping was performed in a facility having a structure shown in FIG. 1 in which the packed tower (packing material=cascade mini-ring) was disposed as the diffusion tower.

Subsequently, into the hydrolysis reaction liquid subjected to the stripping, carbon dioxide was introduced at 0.35 MPaG and 20° C. As a result, methionine was precipitated, and a methionine slurry was obtained.

The methionine slurry was subjected to solid-liquid separation using a centrifugal filter (KOKUSAN Co. Ltd., H-112). Specifically, 600 g of the methionine slurry was poured at 600 g/min into the centrifugal filter rotated at 1700 rpm so that crude methionine stuck to a filter cloth. Subsequently, the number of revolutions was set to 3800 rpm to shake off water for 2 minutes. As a result, the methionine slurry was separated into solid and liquid to obtain a methionine cake and a mother liquor. The pure methionine content in the methionine cake measured was 49.0 g (converted from HPLC measurement).

The methionine cake was washed by spraying washing water for purification and then dried under a slightly reduced pressure at a temperature of 85 to 105° C. to obtain powder methionine as a product (purity=99.6%, yield=97%). The mother liquor was introduced into a concentrator and heated at 115° C. and then 140° C. under an increased pressure of 0.2 MPaG for concentration. Although not described in detail, the concentrated liquid obtained by this concentration was also subjected to crystallization and solid-liquid separation to recover methionine contained in the concentrated liquid. In this mother liquor concentration step, a concentration process gas mainly composed of steam was generated as a process gas.

In Example 1, the stripping for the hydrolysis reaction liquid was performed as follows. First, the hydrolysis reaction liquid was supplied to the upper portion of the diffusion tower. A stripping gas was supplied to the lower portion of the diffusion tower. The process gas and heated steam were supplied as the stripping gas to the gas phase part in the lower portion of the diffusion tower, and the heated steam was supplied as the stripping gas to the liquid phase part. The amount of the process gas supplied to the gas phase part was set to 1.5 mass % of the amount of the hydrolysis reaction liquid supplied to the upper portion of the diffusion tower. The amount of the heated steam supplied to the gas phase part was set to 3.0 mass % of the amount of the hydrolysis reaction liquid supplied. The amount of the heated steam supplied to the liquid phase part was set to 1.5 mass % of the amount of the hydrolysis reaction liquid supplied. The concentration process gas generated in the concentration step was used as the process gas.

Comparative Example 1

The stripping for the hydrolysis reaction liquid was performed by using only the heated steam as the stripping gas with the method of Example 1. In Comparative Example 1, the hydrolysis reaction liquid was supplied to the upper portion of the diffusion tower. In the lower portion of the diffusion tower, heated steam was supplied to each of the gas phase part and the liquid phase part. The amount of the heated steam supplied to the gas phase part was set to 4.6 mass % of the amount of the hydrolysis reaction liquid supplied to the upper portion of the diffusion tower. The amount of the heated steam supplied to the liquid phase part was set to 1.6 mass % of the amount of the hydrolysis reaction liquid supplied to the upper portion of the diffusion tower.

Ammonia Removal Efficiency

The ammonia concentration of the hydrolysis reaction liquid immediately before introduction into the diffusion tower and the ammonia concentration of the hydrolysis reaction liquid immediately after discharge from the diffusion tower were measured. The result is as follows.

Example 1

Ammonia concentration immediately before introduction=8040 ppm
Ammonia concentration immediately after discharge=390 ppm
Ammonia removal rate=95.1%

Comparative Example 1

Ammonia concentration immediately before introduction=7040 ppm
Ammonia concentration immediately after discharge=1200 ppm
Ammonia removal rate=83.0%

In Example 1, the ammonia removal rate is higher than that in Comparative Example 1. The method of Example 1 is excellent in ammonia removal efficiency. This result clearly shows the superiority of the present invention using the process gas as the stripping gas. Therefore, it is clear that the manufacturing method of the present invention can achieve an improvement in the ammonia removal efficiency.

INDUSTRIAL APPLICABILITY

The method for manufacturing methionine described above can provide a technique capable of achieving an improvement in ammonia removal efficiency.

EXPLANATIONS OF LETTERS OR NUMERALS 2 facility
4 diffusion tower
6 emission gas condenser
8 storage tank
10 gas pipe
12 liquid pipe
14 rectification part

The invention claimed is:

1. A method for manufacturing methionine comprising
a hydantoin step of reacting 3-methylmercaptopropionaldehyde and hydrocyanic acid, or a compound obtained by reacting 3-methylmercaptopropionaldehyde and hydrocyanic acid, with carbon dioxide and ammonia to obtain a liquid containing 5-(2-methylmercaptoethyl) hydantoin,
a hydrolysis step of hydrolyzing the 5-(2-methylmercaptoethyl)hydantoin to obtain a liquid containing a methionine salt,
a crystallization step of introducing carbon dioxide into the liquid containing a methionine salt to precipitate methionine, and
a separation step of performing solid-liquid separation of a methionine slurry obtained in the crystallization step into a cake of the methionine and a mother liquor,
the method comprising:
a removal step of supplying the liquid containing a methionine salt obtained in the hydrolysis step to a diffusion tower from an upper portion thereof and supplying a stripping gas to the diffusion tower from a lower portion thereof to remove ammonia contained in the liquid through stripping, wherein
the stripping gas contains a process gas generated in a process of manufacturing methionine.

2. The method according to claim 1, comprising
a bubbling step of blowing an inert gas into the liquid containing 5-(2-methylmercaptoethyl)hydantoin, and
a concentration step of concentrating the mother liquor, wherein
the stripping gas contains at least one process gas selected from the group consisting of a process gas generated in the bubbling step, a process gas generated in the concentration step, and a process gas generated in the hydrolysis step.

3. The method according to claim 2, wherein
the stripping gas contains the process gas generated in the concentration step.

* * * * *